US012624007B2

(12) United States Patent
Oh et al.

(10) Patent No.: US 12,624,007 B2
(45) Date of Patent: May 12, 2026

(54) NAPHTHALIMIDE SULFONATE DERIVATIVE, AND PHOTOACID GENERATOR AND PHOTORESIST COMPOSITION WHICH COMPRISE SAME

(71) Applicant: SAMYANG CORPORATION, Seoul (KR)

(72) Inventors: Chun Rim Oh, Seoul (KR); Dae Hyuk Choi, Seoul (KR); Min Jung Kim, Daejeon (KR); Deuk Rak Lee, Daejeon (KR); Won Jung Lee, Daejeon (KR); Yu Na Choi, Daejeon (KR); Ji Eun Choi, Seongnam-si (KR)

(73) Assignee: SAMYANG CORPORATION, Seoul (KR)

( * ) Notice: Subject to any disclaimer, the term of this patent is extended or adjusted under 35 U.S.C. 154(b) by 472 days.

(21) Appl. No.: 18/028,878

(22) PCT Filed: Sep. 29, 2021

(86) PCT No.: PCT/KR2021/013398

§ 371 (c)(1),
(2) Date: Mar. 28, 2023

(87) PCT Pub. No.: WO2022/071774

PCT Pub. Date: Apr. 7, 2022

(65) Prior Publication Data

US 2023/0331680 A1 Oct. 19, 2023

(30) Foreign Application Priority Data

Sep. 29, 2020 (KR) ........................ 10-2020-0127042

(51) Int. Cl.
*C07D 221/14* (2006.01)
*G03F 7/004* (2006.01)

(52) U.S. Cl.
CPC ......... *C07D 221/14* (2013.01); *G03F 7/0045* (2013.01)

(58) Field of Classification Search
None
See application file for complete search history.

(56) References Cited

U.S. PATENT DOCUMENTS

| | | | |
|---|---|---|---|
| 10,976,658 B2 * | 4/2021 | Zhang .................. | C07D 401/10 |
| 2016/0085148 A1 | 3/2016 | Zhang et al. | |
| 2016/0368879 A1 | 12/2016 | Ikeda et al. | |
| 2020/0183271 A1 | 6/2020 | Miyake et al. | |

FOREIGN PATENT DOCUMENTS

| | | | |
|---|---|---|---|
| CN | 104610046 | A | 5/2015 |
| JP | 2016-89085 | A | 5/2016 |
| JP | 2019-215388 | A | 12/2019 |
| KR | 10-2016-0030210 | A | 3/2016 |
| KR | 10-2017-0042726 | A | 4/2017 |
| KR | 10-2018-0101564 | A | 9/2018 |

OTHER PUBLICATIONS

International Search Report, issued in PCT/KR2021/013398, PCT/ISA/210, dated Dec. 31, 2021.

* cited by examiner

*Primary Examiner* — Po-Chih Chen
(74) *Attorney, Agent, or Firm* — Birch, Stewart, Kolasch & Birch, LLP

(57) ABSTRACT

The present invention relates to a naphthalimide sulfonate derivative, and a photoacid generator and a photoresist composition which comprise same, and, more specifically, to a naphthalimide sulfonate derivative compound, and a photoacid generator and a photoresist composition which comprise same, the compound having an excellent absorbance of light with an i-line wavelength (365 nm), having a high solubility in an organic solvent, having excellent thermal stability, and exhibiting a good acid generation rate.

6 Claims, No Drawings

NAPHTHALIMIDE SULFONATE DERIVATIVE, AND PHOTOACID GENERATOR AND PHOTORESIST COMPOSITION WHICH COMPRISE SAME

TECHNICAL FIELD

The present invention relates to a naphthalimide sulfonic acid derivative, and a photoacid generator and a photoresist composition comprising the same, and more specifically, the present invention relates to a naphthalimide sulfonic acid derivative compound which has an excellent absorbance of light with i-line wavelength (365 nm) and a high solubility in an organic solvent, and exhibits excellent thermal stability and good acid generation rate, and a photoacid generator and a photoresist composition comprising the same.

BACKGROUND ART

A photoacid generator is a compound that generates an acid by light irradiation, and the acid generated therefrom—according to the components in a photoresist composition—decomposes a part of the components in the composition or causes crosslinking reaction, to generate change in polarity of polymer in the composition. Such a change in polarity of polymer brings difference in solubility to developer solution between the exposed part and the unexposed part, and as a result, positive or negative lithography becomes possible.

For a photoresist composition, the photoacid generator therein should have good energy sensitivity to the irradiated light so that micropatterns can be formed. However, use of conventional photoacid generator alone has a problem that the sensitivity of photoresist cannot be increased satisfactorily.

Therefore, it is necessary to develop a photoacid generator which has excellent photosensitivity so as to realize sufficient sensitivity even with a small amount, and thus can reduce exposure dose and increase production due to cost reduction and excellent sensitivity. In addition, improvement in solubility of photoacid generator to the main solvent of photoresist has the advantage of facilitating preparation of various compositions.

Various developments for naphthalimide compound have been made in order to increase photosensitivity and improve solubility thereof. For instance, Korean Laid-open Patent Publication No. 10-2017-0125980 discloses preparation of naphthalimide compound by using a cryogenic condition of −70° C. and metal compound such as 1-butyl lithium, and Korean Laid-open Patent Publication No. 10-2017-0042726 and Korean Laid-open Patent Publication No. 2012-0114353 disclose preparation of naphthalimide compound by using bromine-substituted compound.

Problems to be Solved

The purpose of the present invention is to provide a naphthalimide sulfonic acid derivative compound which has an excellent absorbance of light with i-line wavelength (365 nm) and a high solubility in an organic solvent, and exhibits excellent thermal stability and good acid generation rate, and a photoacid generator and a photoresist composition comprising the same.

Technical Means

In order to achieve the above-stated purpose, the 1$^{st}$ aspect of the present invention provides a naphthalimide sulfonic acid derivative compound represented by the following Formula I or II:

[Formula I]

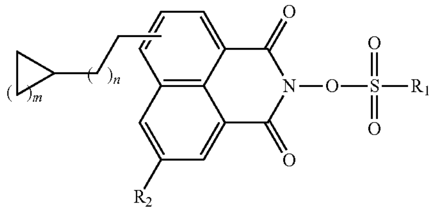

wherein, in Formula I, $R_1$ is a substituted or unsubstituted aliphatic hydrocarbon group, a substituted or unsubstituted aryl group, a substituted or unsubstituted arylalkyl group, or a substituted or unsubstituted alkylaryl group; $R_2$ is hydrogen atom or t-butyl group; m is an integer of 1 to 4; n is an integer of 0 to 2;

[Formula II]

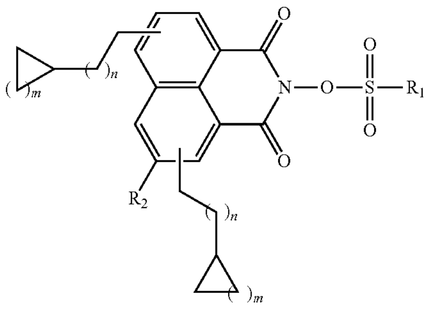

wherein, in Formula II, $R_1$, m and n are the same as defined in Formula I, and $R_2$ is hydrogen atom.

The 2$^{nd}$ aspect of the present invention provides a photoacid generator comprising the naphthalimide sulfonic acid derivative compound of the present invention.

The 3$^{rd}$ aspect of the present invention provides a photoresist composition comprising the naphthalimide sulfonic acid derivative compound of the present invention; and a binder resin.

The 4$^{th}$ aspect of the present invention provides an acenaphthene derivative compound represented by the following Formula III or IV:

[Formula III]

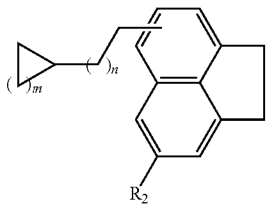

wherein, in Formula III, $R_2$ is hydrogen atom or t-butyl group; m is an integer of 1 to 4; n is an integer of 0 to 2;

[Formula IV]

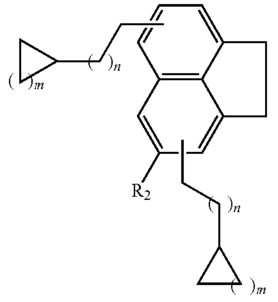

wherein, in Formula IV, $R_2$ is hydrogen atom; and m and n are the same as defined in Formula III.

The $5^{th}$ aspect of the present invention provides a method for preparing an acenaphthene derivative compound represented by the above Formula III or IV, comprising a step of reducing a compound represented by the following Formula III' or IV':

[Formula III']

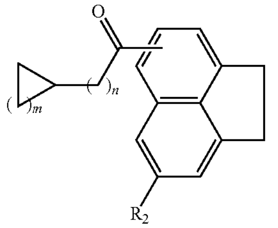

[Formula IV']

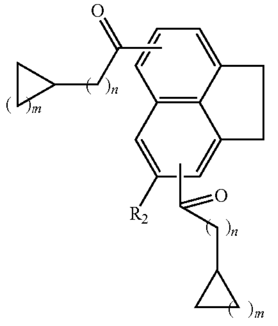

wherein, in Formulas III' and IV', $R_2$, m and n are the same as defined in Formulas III and IV', respectively.

Effect of the Invention

The naphthalimide sulfonic acid derivative compound of the present invention has high solubility in a solvent for photoresist, excellent thermal stability, and very excellent sensitivity to light for photoresist (for example, light with i-line wavelength (365 nm)), and thus, when used as a photoacid generator component in a photoresist composition, it can provide patterns having excellent developability, taper angle, pattern stability, etc. even with a small amount of use, and it also can minimize the outgassing generated from photoacid generator in exposure and post-bake processes, and so it can reduce pollution and has the advantage of minimizing defects that may be generated thereby.

CONCRETE MODE FOR CARRYING OUT THE INVENTION

The present invention is explained in more detail below.

The naphthalimide sulfonic acid derivative compound of the present invention is represented by the following Formula I or II:

[Formula I]

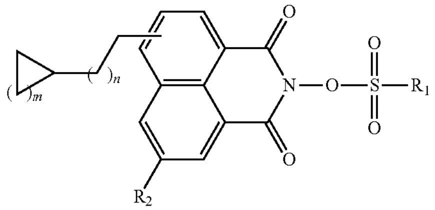

wherein, in Formula I, $R_1$ is a substituted or unsubstituted aliphatic hydrocarbon group, a substituted or unsubstituted aryl group, a substituted or unsubstituted arylalkyl group, or a substituted or unsubstituted alkylaryl group; $R_2$ is hydrogen atom or t-butyl group; m is an integer of 1 to 4; n is an integer of 0 to 2;

[Formula II]

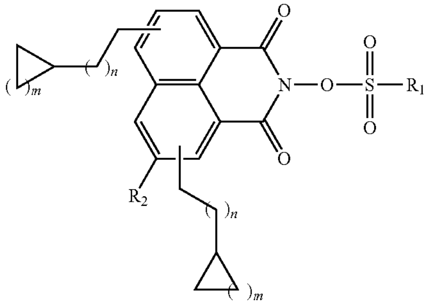

wherein, in Formula II, $R_1$, m and n are the same as defined in Formula I, and $R_2$ is hydrogen atom.

More concretely, in Formulas I and II, $R_1$ may be a substituted or unsubstituted $C_1$-$C_{12}$ linear alkyl group or $C_3$-$C_{12}$ branched alkyl group; a substituted or unsubstituted $C_3$-$C_{12}$ alicyclic hydrocarbon group; a substituted or unsubstituted $C_6$-$C_{20}$ aryl group; a substituted or unsubstituted $C_7$-$C_{20}$ arylalkyl group; or a substituted or unsubstituted $C_7$-$C_{20}$ alkylaryl group.

Still more concretely, in Formulas I and II, $R_1$ may be a $C_1$-$C_{12}$ linear alkyl group or $C_3$-$C_{12}$ branched alkyl group that is unsubstituted or substituted with one or more halogen atoms or alicyclic hydrocarbon group; a $C_3$-$C_{12}$ alicyclic hydrocarbon group that is unsubstituted or substituted with one or more halogen atoms; a $C_6$-$C_{20}$ aryl group that is unsubstituted or substituted with one or more halogen atoms; a $C_7$-$C_{20}$ arylalkyl group that is unsubstituted or substituted with one or more halogen atoms or $C_1$-$C_{12}$ alkylthio group; or a $C_7$-$C_{20}$ alkylaryl group that is unsubstituted or substituted with one or more halogen atoms.

Still more concretely, the above $R_1$ may be methyl group, ethyl group, trifluoromethyl group, 2,2,2-trifluoroethyl group, nonafluorobutyl group or tosyl group.

In the present invention, a substituent comprising "alkyl" moiety includes all forms of linear type or branched type, and "cycloalkyl" includes hydrocarbons of not only single ring system but also multi-ring system. In the present invention, "aryl" is an organic radical derived from aromatic hydrocarbon by removing therefrom one hydrogen, and it includes a single or fused ring system containing suitably 4 to 7, preferably 5 or 6 ring atoms in each ring, and even a form of plural aryls connected by single bonds. Also, in the present invention, $C_1$-$C_{12}$ alkyl group may be more concretely $C_1$-$C_{10}$ alkyl and still more concretely $C_1$-$C_6$ alkyl; $C_6$-$C_{20}$ aryl group may be more concretely $C_6$-$C_{18}$ aryl; and $C_3$-$C_{12}$ cycloalkyl group may be more concretely $C_3$-$C_{10}$ cycloalkyl.

In an embodiment, the naphthalimide sulfonic acid derivative compound of the present invention may be selected from the following compounds, but it is not especially limited thereto.

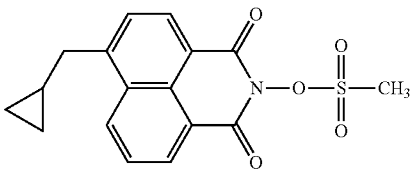

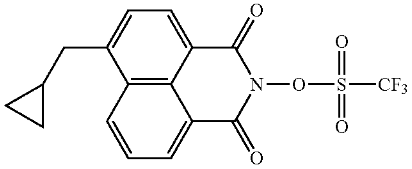 [SMILES: O=C1c2cccc3c(CC4CC4)ccc(c23)C(=O)N1OS(=O)(=O)C(F)(F)F]

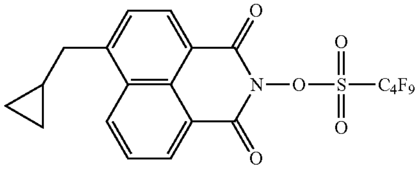

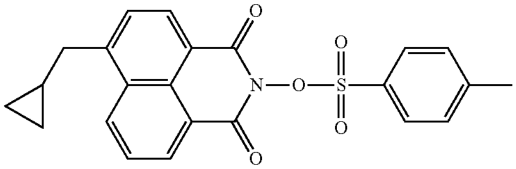

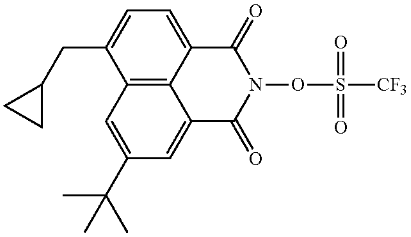

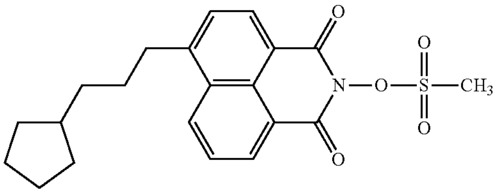

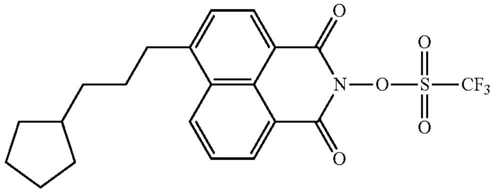

-continued

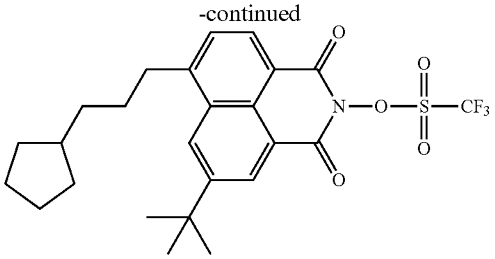

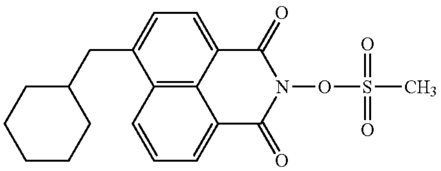

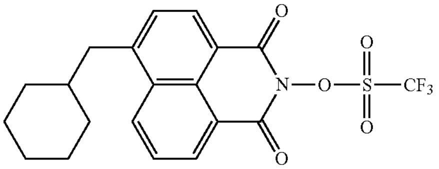

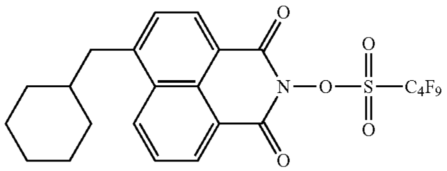

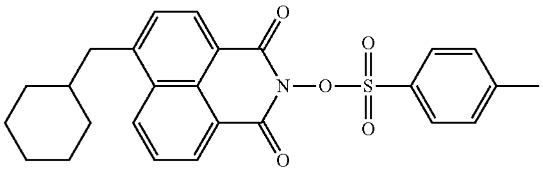

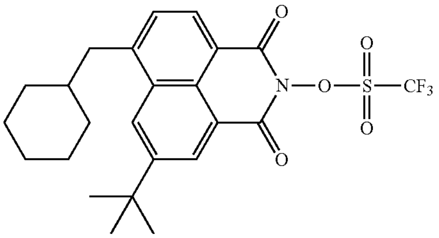

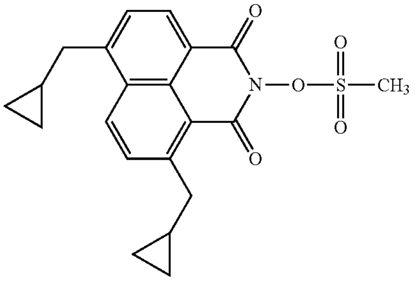

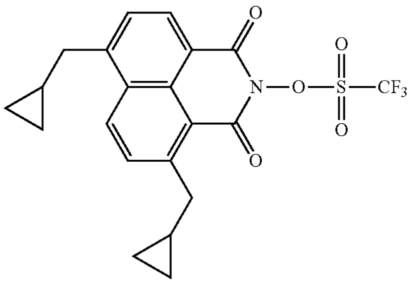

-continued

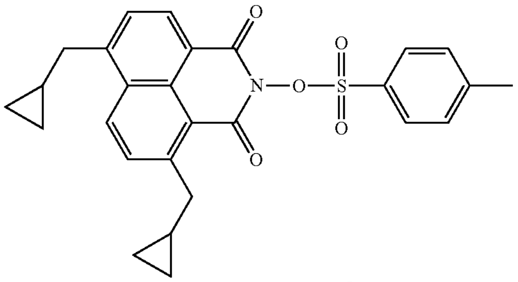

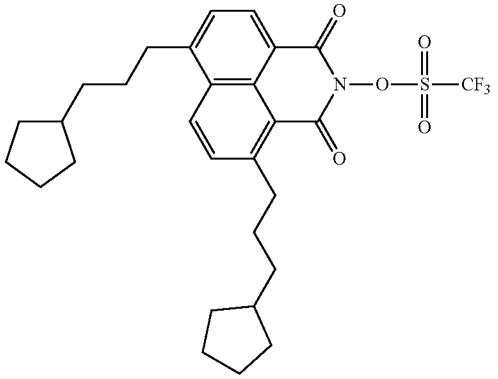

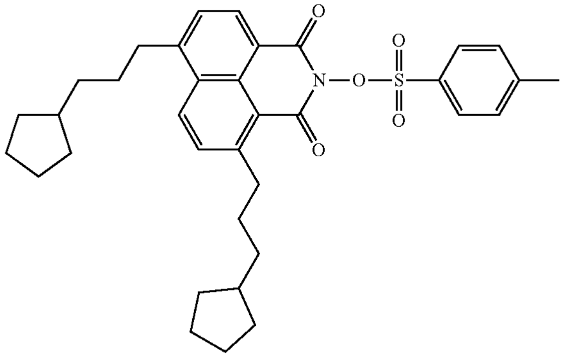

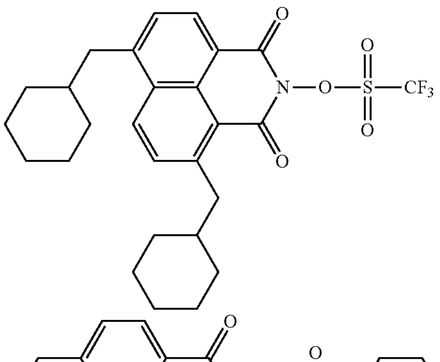

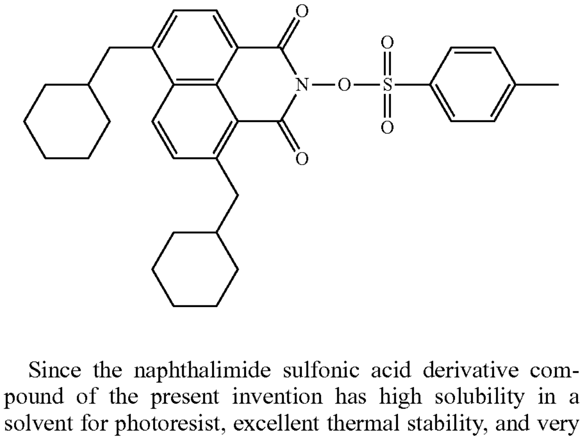

Since the naphthalimide sulfonic acid derivative compound of the present invention has high solubility in a solvent for photoresist, excellent thermal stability, and very excellent sensitivity to light for photoresist, it is very useful as a photoacid generator component in a photoresist composition.

Therefore, other aspects of the present invention provide a photoacid generator and a photoresist composition comprising the naphthalimide sulfonic acid derivative compound of the present invention.

The photoresist composition of the present invention comprises the naphthalimide sulfonic acid derivative compound of the present invention; and a binder resin, wherein the naphthalimide sulfonic acid derivative compound is comprised as a component for photoacid generation.

In an embodiment, the binder resin may be selected from, for example, polymers of hydroxystyrene or derivatives thereof; polymers of acrylic acid or derivatives thereof; polymers of methacrylic acid or derivatives thereof; copolymers of two or more monomers selected from hydroxystyrene, acrylic acid, methacrylic acid, and derivatives thereof; copolymers of two or more monomers selected from hydroxystyrene, styrene, and derivatives thereof; copolymers of three or more monomers selected from cycloolefins, maleic anhydride, acrylic acid, and derivatives thereof; copolymers of three or more monomers selected from cycloolefins, maleimides, acrylic acid, and derivatives thereof; polynorbornene; metathesis ring-opening polymers; and polymers partially substituted with acid labile group having alkali dissolution control ability in said polymers; and combinations thereof, but it is not especially limited thereto. Examples of the acid labile group incorporated into the polymer may include tertiary alkyl group, trialkylsilyl group, oxoalkyl group, aryl-substituted alkyl group, heteroalicyclic group such as tetrahydropyran-2-yl group, etc., tertiary alkylcarbonyl group, tertiary alkylcarbonylalkyl group, alkyloxycarbonyl groups, etc.

In an embodiment, the binder resin may be selected from, for example, polymers of hydroxystyrene or derivatives thereof; polymers of acrylic acid or derivatives thereof; polymers of methacrylic acid or derivatives thereof; copolymers of two or more monomers selected from hydroxystyrene, acrylic acid, methacrylic acid, and derivatives thereof; copolymers of two or more monomers selected from hydroxystyrene, styrene, and derivatives thereof; copolymers of three or more monomers selected from hydroxystyrene, styrene, acrylic acid, olefins, cycloolefins, maleic anhydride and derivatives thereof; and combinations thereof, but it is not especially limited thereto.

In an embodiment, said "derivative" may be, for example, alkyl or alkoxy-substituted form (more concretely, $C_1$-$C_{10}$ alkyl or alkoxy-substituted form) of the original compound, or if the original compound is an acid compound, it may be alkyl ester (more concretely, $C_1$-$C_{10}$ alkyl ester) of the original compound, but it is not especially limited thereto.

In an embodiment, the binder resin may be, for example, a copolymer of two or more monomers selected from the following monomers:

methyl (meth)acrylate, ethyl (meth)acrylate, propyl (meth)acrylate, butyl (meth)acrylate, pentyl (meth) acrylate, hexyl (meth)acrylate, cyclohexyl (meth)acrylate, heptyl (meth)acrylate, octyl (meth)acrylate, nonyl (meth)acrylate, decyl (meth)acrylate, lauryl (meth) acrylate, dodecyl (meth)acrylate, tetradecyl (meth) acrylate hexadecyl (meth)acrylate, isobornyl (meth) acrylate, adamantyl (meth)acrylate, dicyclopentanyl (meth)acrylate, dicyclopentenyl (meth)acrylate, benzyl (meth)acrylate, 2-methoxyethyl (meth)acrylate, 2-ethoxyethyl (meth)acrylate, acrylic acid, methacrylic acid, itaconic acid, maleic acid, maleic anhydride, maleic acid monoalkyl ester, monoalkyl itaconate, monoalkyl fumarate, glycidyl acrylate, glycidyl methacrylate, 3,4-epoxybutyl (meth)acrylate, 2,3-epoxycyclohexyl (meth)acrylate, 3,4-epoxycyclohexylmethyl (meth)acrylate, 3-methyloxetane-3-methyl (meth)acrylate, 3-ethyloxetane-3-methyl (meth)acrylate, etc. and styrene, α-methylstyrene, acetoxystyrene, N-methylmaleimide, N-ethylmaleimide, N-propylmaleimide, N-butylmaleimide, N-cyclohexylmaleimide, (meth) acrylamide, N-methyl (meth)acrylamide.

In an embodiment, the binder resin may be a polymer having acryl unsaturated bond in its side chain, and this may be, for example, a copolymer obtained by addition reaction of epoxy compound to a copolymer containing carboxylic acid.

More concretely, the copolymer containing carboxylic acid may be obtained by copolymerizing a monomer containing carboxylic acid such as acrylic acid, methacrylic acid, itaconic acid, maleic acid, maleic acid monoalkyl ester, etc. and one or monomers of alkyl (meth)acrylates such as methyl (meth)acrylate, hexyl (meth)acrylate, etc., cyclohexyl (meth)acrylate, isobornyl (meth)acrylate, adamantyl (meth)acrylate, dicyclopentanyl (meth)acrylate, dicyclopentenyl (meth)acrylate, benzyl (meth)acrylate, 2-methoxyethyl (meth)acrylate, 2-ethoxyethyl (meth)acrylate, styrene, a-methylstyrene, acetoxystyrene, N-methylmaleimide, N-ethylmaleimide, N-propylmaleimide, N-butylmaleimide, N-cyclohexylmaleimide, (meth)acrylamide, N-methyl (meth)acryl amide, etc., and a copolymer obtained by addition reaction of epoxy compound such as glycidyl acrylate, glycidyl methacrylate, 3,4-epoxybutyl (meth)acrylate, 2,3-epoxycyclohexyl (meth)acrylate, 3,4-epoxycyclohexylmethyl (meth)acrylate, etc. to such a carboxylic acid-containing copolymer at a temperature of 40 to 180° C. may be used as the binder resin.

In an embodiment, the weight average molecular weight of the binder resin may be 2,000 to 300,000 and more concretely 4,000 to 100,000, and dispersity thereof may be 1 to 10, but it is not especially limited thereto.

In an embodiment, in order to increase developability and minimize exposure dose, the naphthalimide sulfonic acid derivative compound used as an acid generator may be comprised, based on 100 weight % of the photoresist composition of the present invention, in an amount of: 0.01 to 10 weight %, 0.01 to 9 weight %, 0.01 to 8 weight %, 0.01 to 7 weight %, 0.01 to 6 weight %, 0.01 to 5 weight %, 0.01 to 4 weight %, 0.01 to 3 weight %, 0.01 to 2 weight %, 0.01 to 1 weight %, 0.01 to 0.5 weight %, 0.01 to 0.4 weight %, 0.01 to 0.35 weight %, 0.01 to 0.3 weight %, 0.01 to 0.2 weight %, 0.05 to 10 weight %, 0.05 to 9 weight %, 0.05 to 8 weight %, 0.05 to 7 weight %, 0.05 to 6 weight %, 0.05 to 5 weight %, 0.05 to 4 weight %, 0.05 to 3 weight %, 0.05 to 2 weight %, 0.05 to 1 weight %, 0.05 to 0.5 weight %, 0.05 to 0.4 weight %, 0.05 to 0.35 weight %, 0.05 to 0.3 weight %, 0.05 to 0.2 weight %, 0.1 to 10 weight %, 0.1 to 9 weight %, 0.1 to 8 weight %, 0.1 to 7 weight %, 0.1 to 6 weight %, 0.1 to 5 weight %, 0.1 to 4 weight %, 0.1 to 3 weight %, 0.1 to 2 weight %, 0.1 to 1 weight %, 0.1 to 0.5 weight %, 0.1 to 0.4 weight %, 0.1 to 0.35 weight %, 0.1 to 0.3 weight %, 0.1 to 0.2 weight %, 0.2 to 10 weight %, 0.2 to 9 weight %, 0.2 to 8 weight %, 0.2 to 7 weight %, 0.2 to 6 weight %, 0.2 to 5 weight %, 0.2 to 4 weight %, 0.2 to 3 weight %, 0.2 to 2 weight %, 0.2 to 1 weight %, 0.2 to 0.5 weight %, 0.2 to 0.4 weight %, 0.2 to 0.35 weight %, 0.2 to 0.3 weight %, 0.25 to 10 weight %, 0.25 to 9 weight %, 0.25 to 8 weight %, 0.25 to 7 weight %, 0.25 to 6 weight %, 0.25 to 5 weight %, 0.25 to 4 weight %, 0.25 to 3 weight %, 0.25 to 2 weight %, 0.25 to 1 weight %, 0.25 to 0.5 weight %, 0.25 to 0.4 weight %, 0.25 to 0.35 weight %, 0.25 to 0.3 weight %, 0.3 to 10 weight %, 0.3 to 9 weight %, 0.3 to 8 weight %, 0.3 to 7 weight %, 0.3 to 6 weight %, 0.3 to 5 weight %, 0.3 to 4 weight %, 0.3 to 3 weight %, 0.3 to 2 weight %, 0.3 to 1 weight %, 0.3 to 0.5 weight %, 0.3 to 0.4 weight %, 0.3 to 0.35 weight %, 0.35 to 10 weight %, 0.35 to 9 weight %, 0.35 to 8 weight %, 0.35 to 7 weight %, 0.35 to 6 weight %, 0.35 to 5 weight %, 0.35 to 4 weight %, 0.35 to 3 weight %, 0.35 to 2 weight %, 0.35 to 1 weight %, 0.35 to 0.5 weight %, 0.35 to 0.4 weight %, 0.4 to 10 weight %, 0.4 to 9 weight %, 0.4 to 8 weight %, 0.4 to 7 weight %, 0.4 to 6 weight %, 0.4 to 5 weight %, 0.4 to 4 weight %, 0.4 to 3 weight %, 0.4 to 2 weight %, 0.4 to 1 weight %, 0.4 to 0.5 weight %, and more concretely in an amount of 0.1 to 5 weight %, but it is not especially limited thereto.

In an embodiment, in order to control pattern characteristics and give thin film properties, the binder resin may be comprised, based on 100 weight % of the photoresist composition of the present invention, in an amount of: for example, 30 to 99 weight %, 35 to 99 weight %, 40 to 99 weight %, 45 to 99 weight %, 50 to 99 weight %, 30 to 97 weight %, 35 to 97 weight %, 40 to 97 weight %, 45 to 97 weight %, 50 to 97 weight %, 30 to 95 weight %, 35 to 95 weight %, 40 to 95 weight %, 45 to 95 weight %, 50 to 95 weight %, 30 to 93 weight %, 35 to 93 weight %, 40 to 93 weight %, 45 to 93 weight %, 50 to 93 weight %, 30 to 90 weight %, 35 to 90 weight %, 40 to 90 weight %, 45 to 90 weight %, 50 to 90 weight %, 30 to 85 weight %, 35 to 85 weight %, 40 to 85 weight %, 45 to 85 weight %, 50 to 85 weight %, 30 to 80 weight %, 35 to 80 weight %, 40 to 80 weight %, 45 to 80 weight %, 50 to 80 weight %, 30 to 75 weight %, 35 to 75 weight %, 40 to 75 weight %, 45 to 75 weight %, 50 to 75 weight %, 30 to 70 weight %, 35 to 70 weight %, 40 to 70 weight %, 45 to 70 weight %, 50 to 70 weight %, 30 to 65 weight %, 35 to 65 weight %, 40 to 65 weight %, 45 to 65 weight %, 50 to 65 weight %, 30 to 60 weight %, 35 to 60 weight %, 40 to 60 weight %, 45 to 60 weight %, 50 to 60 weight %, 30 to 55 weight %, 35 to 55 weight %, 40 to 55 weight %, 45 to 55 weight %, 50 to 55 weight %, and more concretely in an amount of 50 to 99 weight %, but it is not especially limited thereto.

The photoresist composition of the present invention may further comprise a solvent.

As the solvent, considering compatibility with the photoacid generator and other compounds, a solvent such as ethyl acetate, butyl acetate, diethylene glycol dimethyl ether, diethylene glycol methyl ethyl ether, methyl methoxy propionate, ethyl ethoxy propionate (EEP), ethyl lactate, propylene glycol monomethyl ether acetate (PGMEA), propylene glycol methyl ether propionate (PGMEP), propylene glycol methyl ether, propylene glycol propyl ether, methyl cellosolve acetate, ethyl cellosolve acetate, diethylene glycol methyl acetate, diethylene glycol ethyl acetate, acetone, methyl isobutyl ketone, cyclohexanone, dimethylformamide (DMF), N,N-dimethylacetamide (DMAc), N-methyl-2-pyrrolidone (NMP), γ-butyrolactone, diethyl ether, ethylene glycol dimethyl ether, diglyme, tetrahydrofuran (THF), methanol, ethanol, propanol, iso-propanol, methyl cellosolve, ethyl cellosolve, diethylene glycol methyl ether, diethylene glycol ethyl ether, dipropylene glycol methyl ether, toluene, xylene, hexane, heptane, octane, etc. may be used alone or in a mixture of two or more thereof.

In an embodiment, in order to adjust the viscosity of the composition to be in the range of 1 to 50 cps, the solvent may be contained, for example, in an amount of 0.9 to 60 weight % in 100 weight % of the photoresist composition of the present invention, but it is not especially limited thereto.

If necessary, the photoresist composition of the present invention may further comprise an additive with compatibility such as defoaming agent, leveling agent, etc.

In an embodiment, the naphthalimide sulfonic acid derivative compound represented by the above Formula I may be prepared as shown in the following Reaction Scheme 1, and the naphthalimide sulfonic acid derivative compound represented by the above Formula II may be prepared as shown in the following Reaction Scheme 2.

[In the above Reaction Schemes 1 and 2, $R_1$, $R_2$, m and n are the same as defined in the above Formulas I and II, respectively.]

Therefore, another aspect of the present invention provides, as an intermediate in the preparation of the naphthalimide sulfonic acid derivative compound of the present invention, an acenaphthene derivative compound represented by the following Formula III or IV and a method for preparing the same:

[Reaction Scheme 1]

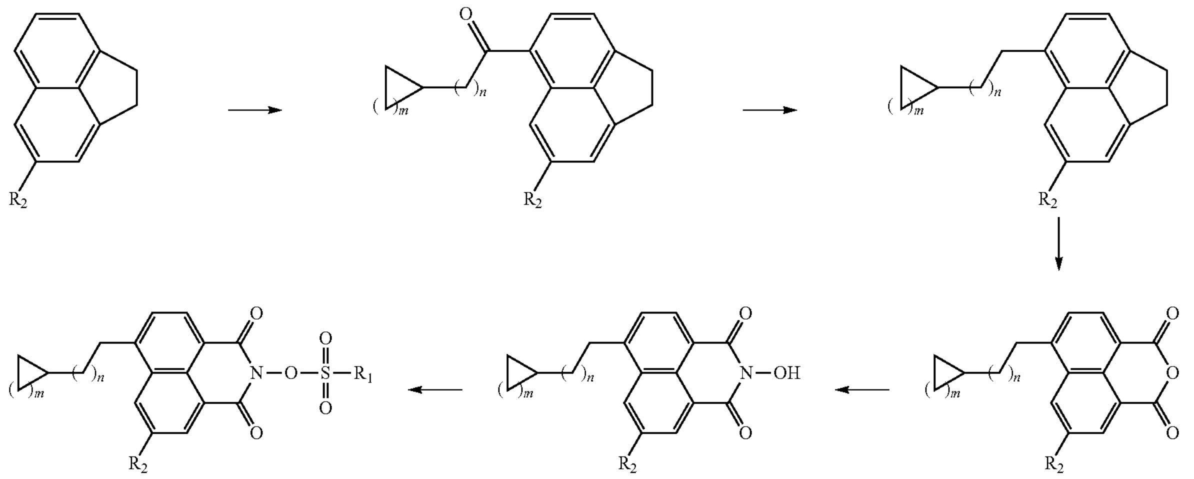

[Reaction Scheme 2]

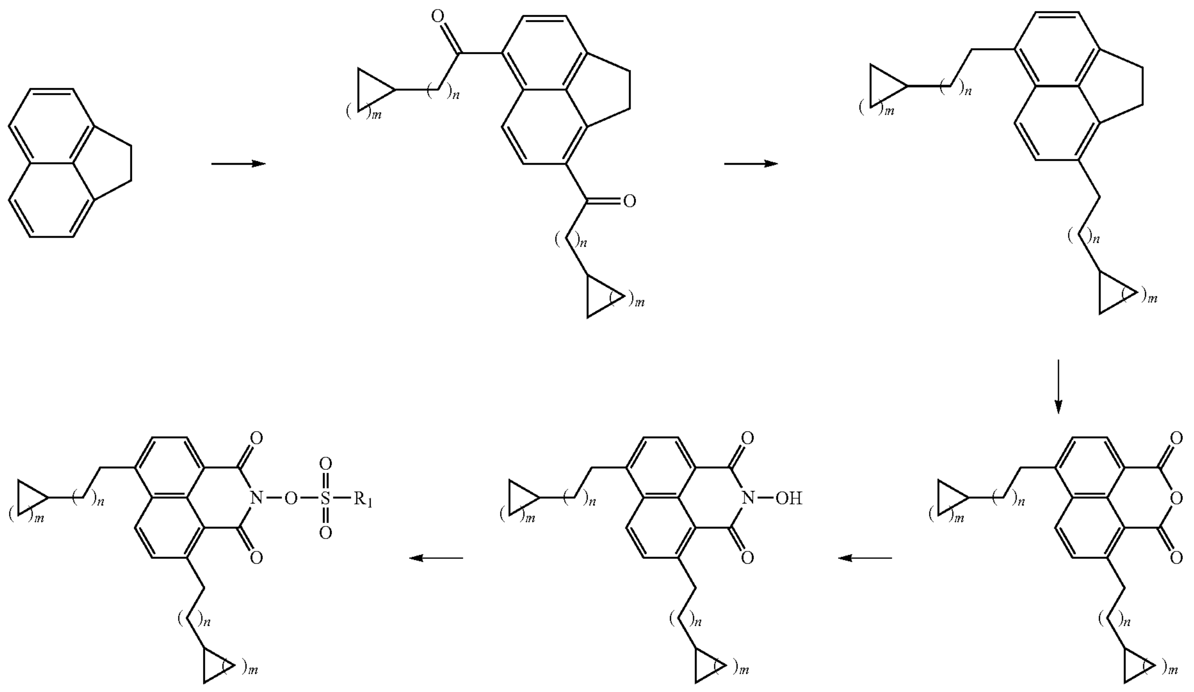

[Formula III]

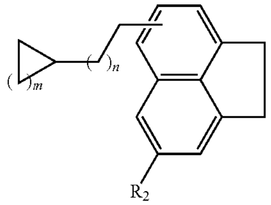

wherein, in Formula III, $R_2$ is hydrogen atom or t-butyl group; m is an integer of 1 to 4; n is an integer of 0 to 2;

[Formula IV]

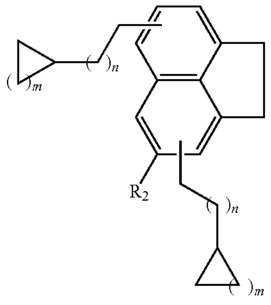

wherein, in Formula IV, $R_2$ is hydrogen atom; and m and n are the same as defined in Formula III.

The method for preparing the above acenaphthene derivative compound represented by Formula III or IV according to the present invention comprises a step of reducing a compound represented by the following Formula III' or IV', respectively:

[Formula III']

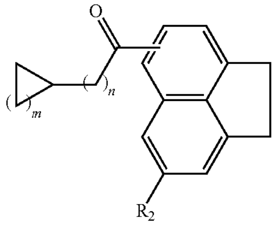

[Formula IV']

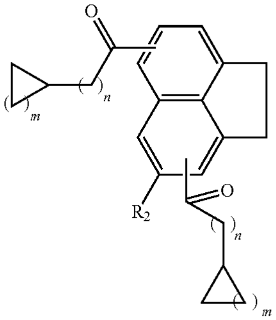

wherein, in Formulas III' and IV', $R_2$, m and n are the same as defined in the above Formulas III and IV', respectively.

In an embodiment, the reduction step may be conducted, for example, in the presence of potassium hydroxide, sodium hydroxide, potassium t-butoxide or a combination thereof, at a high temperature, for example, a temperature of from 100 to 180° C.

The present invention is explained in more detail through the following Examples and Comparative Examples. However, the scope of the present invention is not limited thereby in any manner.

EXAMPLES

Example 1: Preparation of 4-cyclopropanemethyl-naphthalimide trifluoromethane sulfonate (1)

Reaction 1. Synthesis of 5-cyclopropanecarbonyl acenaphthene 5.0 g (32.4 mmol) of acenaphthene was added to dichloromethane, and cooled to 10° C. or lower. 4.55 g (34.0 mmol) of aluminum chloride was added thereto and stirred for 30 minutes, and then 3.39 g (32.4 mmol) of cyclopropanecarbonyl chloride diluted in dichloromethane was slowly added thereto, and the reaction mixture was stirred for 1 hour at 5° C. or less. Next, distilled water was added to the reaction product, and after stirring for 30 minutes, the organic layer was separated. The separated organic layer was washed twice with distilled water, and the collected organic layer was dried with anhydrous magnesium sulfate, and the solvent was removed by distillation under reduced pressure. The concentrated residue was purified by silica gel column chromatography (developing solvent; ethyl acetate:n-heptane=1:4) to obtain 6.03 g (83.7%) of 5-cyclopropanecarbonyl acenaphthene.

$^1$H NMR ($\delta_{ppm}$; $CDCl_3$): 1.08-1.02 (2H, m), 1.31-1.35 (2H, m), 2.63-2.74 (1H, m)), 3.40 (4H, m), 7.31-7.36 (2H, m), 7.51-7.56 (1H, dd), 8.10-8.12 (1H, d), 8.42-8.44 (1H, d)

MS (m/z): 222

Reaction 2. Synthesis of 5-cyclopropylmethyl acenaphthene 5.75 g (25.9 mmol) of 5-cyclopropanecarbonyl acenaphthene, 3.50 g (38.8 mmol) of methyl carbazate, and 4.66 g (77.6 mmol) of acetic acid were dissolved in ethanol, and the reaction mixture was heated to reflux. The reaction mixture was then cooled to room temperature and ethanol was removed under reduced pressure. Ethyl acetate and distilled water were added to the concentrated residue, and after stirring, the organic layer was separated. The separated organic layer was washed twice with distilled water, and the collected organic layer was dried with anhydrous magnesium sulfate, and the solvent was removed by distillation under reduced pressure. The concentrated residue was added to 7.27 g (129.5 mmol) of potassium hydroxide and triethylene glycol, heated to 140° C., stirred, cooled to room temperature, and stirred with n-heptane and distilled water, and then the organic layer was separated. The separated organic layer was washed twice with distilled water, and the collected organic layer was dried with anhydrous magnesium sulfate, and the solvent was removed by distillation under reduced pressure. The product obtained by distilling the organic layer under reduced pressure was purified by silica gel column chromatography (developing solvent: n-heptane alone) to obtain 4.24 g (65.4%) of solid 5-cyclopropylmethyl acenaphthene.

$^1$H NMR ($\delta_{ppm}$; $CDCl_3$): 0.23-0.27 (2H, m) 0.52-0.56 (2H, m), 1.12-1.20 (1H, m), 2.93-2.94 (2H, d) 3.35-3.42

(4H, m), 7.21-7.24 (1H, d) 7.27-7.28 (1H, d), 7.37-7.39 (1H, d), 7.44-7.47 (1H, dd), 7.71-7.73 (1H, d)

MS(m/z): 208

Reaction 3. Synthesis of 4-cyclopropylmethyl naphthylic anhydride 15.0 g (72.0 mmol) of 5-cyclopropylmethyl acenaphthene was added to acetic acid, 107.3 g (360.1 mmol) of sodium dichromate dihydrate was added thereto, and the mixture was stirred at room temperature and heated to reflux. Then, after cooling to room temperature, the reaction mixture was poured into ice water. The generated solid was filtered and washed sequentially with distilled water and ethanol. The resulting solid was dried to obtain 13.70 g (75.4%) of 4-cyclopropylmethyl naphthylic anhydride.

$^1$H NMR ($\delta_{ppm}$; $CDCl_3$): 0.31-0.36 (2H, m), 0.64-0.70 (2H, m), 1.14-1.23 (1H, m), 3.14-3.16 (2H, d), 7.82-7.86 (2H, m), 8.51-8.54 (1H, dd), 8.58-8.60 (1H, d), 8.63-8.65 (1H, dd)

MS(m/z): 252

Reaction 4. Synthesis of N-hydroxy-4-cyclopropylmethyl naphthalimide 13.40 g (53.1 mmol) of 4-cyclopropylmethyl naphthylic anhydride was added to ethanol, 5.54 g (79.7 mmol) of hydroxylamine hydrochloride salt and 6.30 g (79.7 mmol) of pyridine were added thereto, and the mixture was heated to reflux. Ethanol was removed under reduced pressure to obtain 13.30 g (crude yield: 93.7%) of crude N-hydroxy-4-cyclopropylmethyl naphthalimide, which was used in the next reaction without further purification.

$^1$H NMR ($\delta_{ppm}$; $CDCl_3$): 0.30-0.34 (2H, m), 0.64-0.69 (2H, m), 1.12-1.21 (1H, m), 3.14-3.16 (2H, d), 7.79-7.84 (2H, m), 8.49-8.51 (1H, d), 8.61-8.63 (1H, d) 8.67-8.69 (1H, d), 8.72 (1H, b)

MS(m/z): 267

Reaction 5. Synthesis of 4-cyclopropanemethyl-naphthalimide trifluoromethane sulfonate (1)

13.75 g (51.4 mmol) of N-hydroxy-5-cyclopropylmethyl naphthalimide was added to dichloromethane, and 10.41 g (102.9 mmol) of triethylamine was added thereto, and the mixture was stirred for 30 minutes and cooled to 5° C. or lower. After adding 8.67 g (51.4 mmol) of trifluoromethane sulfonyl chloride, the mixture was stirred at room temperature. Then, after adding thereto distilled water and stirring, the organic layer was separated. The separated organic layer was washed twice with distilled water, and the collected organic layer was dried with anhydrous magnesium sulfate, and the solvent was removed by distillation under reduced pressure. The product obtained by distilling the organic layer under reduced pressure was purified by silica gel column chromatography (developing solvent: ethyl acetate:n-heptane=1:4) to obtain 16.24 g (79.1%) of 4-cyclopropanemethyl-naphthalimide trifluoromethane sulfonate (1).

$^1$H NMR ($\delta_{ppm}$; $CDCl_3$): 0.31-0.35 (2H, m), 0.65-0.70 (2H, m), 1.13-1.21 (1H, m), 3.15-3.16 (2H, d), 7.83-7.87 (2H, m), 8.54-8.56 (1H, dd), 8.62-8.64 (1H, d), 8.67-8.69 (1H, dd)

MS(m/z): 399

The following compounds were prepared in the same manner as in Example 1.

| Compound No. | Structure | 1H-NMR | MS (m/z) |
|---|---|---|---|
| 1 | 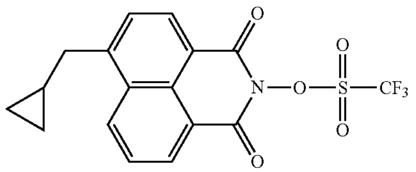 | 0.31-0.35(2H, m), 0.65-0.70(2H, m), 1.13-1.21(1H, m), 3.15-3.16(2H, d), 7.83-7.87(2H, m), 8.54-8.56(1H, dd), 8.62-8.64(1H, d), 8.67-8.69(1H, dd) | 399 |
| 2 | 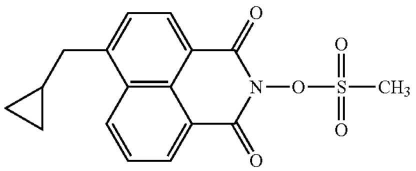 [SMILES: CS(=O)(=O)ON1C(=O)c2cccc3c(CC4CC4)ccc(c23)C1=O] | 0.31-0.35(2H, m), 0.65-0.70(2H, m), 1.13-1.21(1H, m), 3.15-3.16(2H, d), 3.52(3H, s), 7.83-7.87(2H, m), 8.54-8.56(1H, dd), 8.62-8.64(1H, d), 8.67-8.69(1H, dd) | 345 |
| 3 | 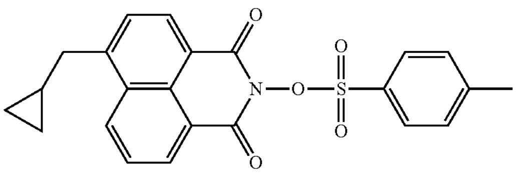 [SMILES: Cc1ccc(S(=O)(=O)ON2C(=O)c3cccc4c(CC5CC5)ccc(c34)C2=O)cc1] | 0.31-0.35(2H, m), 0.65-0.70(2H, m), 1.13-1.21(1H, m), 2.86(3H, s) 3.15-3.16(2H, d), 7.48-7.53(2H, d), 7.75-7.80(2H, d), 7.83-7.87(2H, m), 8.54-8.56(1H, dd), 8.62-8.64(1H, d), 8.67-8.69(1H, dd) | 421 |
| 4 | 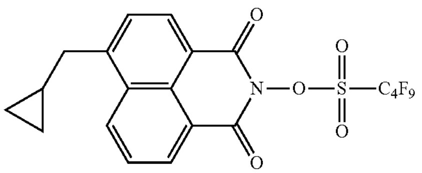 | 0.31-0.35(2H, m), 0.65-0.70(2H, m), 1.13-1.21(1H, m), 3.15-3.16(2H, d), 7.83-7.87(2H, m), 8.54-8.56(1H, dd), 8.62-8.64(1H, d), 8.67-8.69(1H, dd) | 549 |

-continued

| Compound No. | Structure | 1H-NMR | MS (m/z) |
|---|---|---|---|
| 5 | 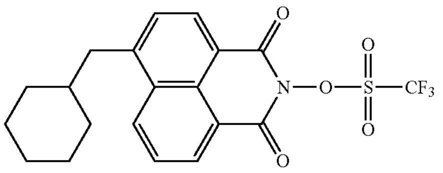 [SMILES: O=C1c2cccc3c(CC4CCCCC4)ccc(c23)C(=O)N1OS(=O)(=O)C(F)(F)F] | 1.06-1.25(5H, m), 1.65-1.71(6H, m), 3.08-3.10(2H, d), 7.61-7.63(1H, d), 7.83-7.87(1H, dd), 8.50-8.52(1H, dd), 8.59-8.61(1H, d), 8.69-8.71(1H, dd) | 441 |
| 6 | 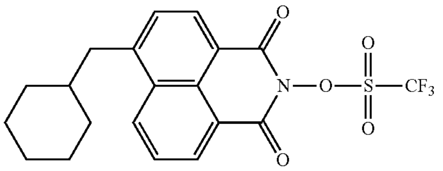 [SMILES: O=C1c2cccc3c(CC4CCCCC4)ccc(c23)C(=O)N1OS(=O)(=O)C(F)(F)F] | 1.06-1.25(5H, m), 1.65-1.71(6H, m), 3.08-3.10(2H, d), 3.54(3H, s), 7.61-7.63(1H, d), 7.83-7.87(1H, dd), 8.50-8.52(1H, dd), 8.59-8.61(1H, d), 8.69-8.71(1H, dd) | 387 |
| 7 | 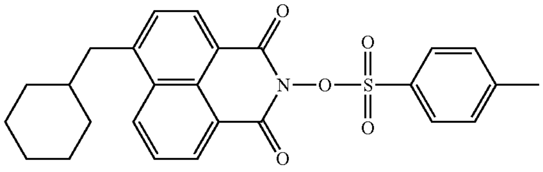 [SMILES: Cc1ccc(S(=O)(=O)ON2C(=O)c3cccc4c(CC5CCCCC5)ccc(c34)C2=O)cc1] | 1.06-1.25(5H, m), 1.65-1.71(6H, m), 2.90(3H, s), 3.08-3.10(2H, d), 7.49-7.54(2H, d), 7.75-7.79(2H, d), 7.61-7.63(1H, d), 7.83-7.87(1H, dd), 8.50-8.52(1H, dd), 8.59-8.61(1H, d), 8.69-8.71(1H, dd) | 463 |
| 8 | 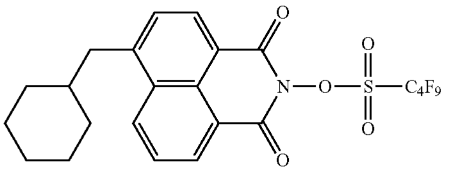 | 1.06-1.25(5H, m), 1.65-1.71(6H, m), 3.08-3.10(2H, d), 7.61-7.63(1H, d), 7.83-7.87(1H, dd), 8.50-8.52(1H, dd), 8.59-8.61(1H, d), 8.69-8.71(1H, dd) | 591 |
| 9 | 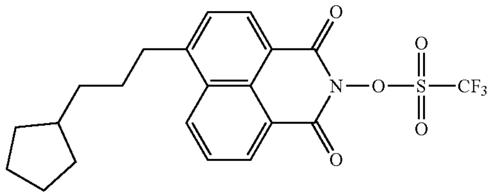 [SMILES: O=C1c2cccc3c(CCCC4CCCC4)ccc(c23)C(=O)N1OS(=O)(=O)C(F)(F)F] | 1.04-1.12(2H, m), 1.43-1.54(4H, m), 1.54-1.63(2H, m), 1.73-1.85(5H, m), 3.19-3.23(2H, t), 7.67-7.68(1H, d), 7.83-7.87(1H, dd), 8.51-8.54(1H, dd), 8.60-8.62(1H, d), 8.69-8.71(1H, dd) | 455 |
| 10 | 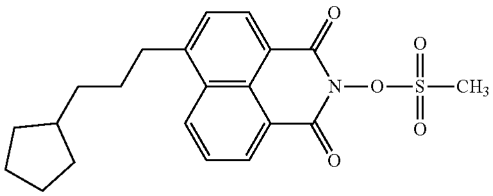 [SMILES: CS(=O)(=O)ON1C(=O)c2cccc3c(CCCC4CCCC4)ccc(c23)C1=O] | 1.04-1.12(2H, m), 1.43-1.54(4H, m), 1.54-1.63(2H, m), 1.73-1.85(5H, m), 3.19-3.23(2H, t), 3.53(3H, s), 7.67-7.68(1H, d), 7.83-7.87(1H, dd), 8.51-8.54(1H, dd), 8.60-8.62(1H, d), 8.69-8.71(1H, dd) | 401 |

Example 2: Preparation of 2,5-dicyclopropanemethyl-naphthalimide trifluoromethane sulfonate (9)

Reaction 1. Synthesis of 3,6-cyclohexanecarbonyl acenaphthene 6.0 g (38.9 mmol) of acenaphthene was added to dichloromethane, and cooled to 10° C. or lower. 10.89 g (81.7 mmol) of aluminum chloride was added thereto and stirred for 30 minutes, and then 12.55 g (85.6 mmol) of cyclohexane chloride diluted in dichloromethane was slowly added thereto, and the reaction mixture was stirred for 1 hour at 5° C. or less. Next, distilled water was added to the reaction product, and after stirring for 30 minutes, the organic layer was separated. The separated organic layer was washed twice with distilled water, and the collected organic layer was dried with anhydrous magnesium sulfate, and the solvent was removed by distillation under reduced pressure. The concentrated residue was purified by silica gel column chromatography (developing solvent; ethyl acetate:n-heptane=1:4) to obtain 10.30 g (70.7%) of 3,6-dicyclohexanecarbonyl acenaphthene.

$^1H$ NMR ($\delta_{ppm}$; $CDCl_3$): 1.08-1.02 (2H, m), 1.31-1.35 (2H, m), 2.63-2.74 (1H, m)), 3.41-3.48 (2H, t), 3.78-3.85 (2H, t) 7.36-7.41 (2H, m), 8.13-8.15 (1H, d), 8.45-8.47 (1H, d)

MS(m/z): 290

Reaction 2. Synthesis of 3,6-dicyclohexylmethyl acenaphthene 10.75 g (28.0 mmol) of 3,6-dicyclohexanecarbonyl acenaphthene, 7.58 g (84.1 mmol) of methyl carbazate, and 10.10 g (168.2 mmol) of acetic acid were dissolved in ethanol, and the reaction mixture was heated to reflux. The reaction mixture was then cooled to room temperature and ethanol was removed under reduced pressure. Ethyl acetate and distilled water were added to the concentrated residue, and after stirring, the organic layer was separated. The separated organic layer was washed twice with distilled water, and the collected organic layer was dried with anhydrous magnesium sulfate, and the solvent was removed by distillation under reduced pressure. The concentrated residue was added to 15.71 g (280.0 mmol) of potassium hydroxide and triethylene glycol, heated to 140° C., stirred, cooled to room temperature, and stirred with n-heptane and distilled water, and then the organic layer was separated. The separated organic layer was washed twice with distilled water, and the collected organic layer was dried with anhydrous magnesium sulfate, and the solvent was removed by distillation under reduced pressure. The product obtained by distilling the organic layer under reduced pressure was purified by silica gel column chromatography (developing solvent: ethyl acetate:n-heptane=1:4) to obtain 4.27 g (58.2%) of 3,6-dicyclohexylmethyl acenaphthene.

$^1$H NMR ($\delta_{ppm}$; $CDCl_3$): 0.23-0.27 (4H, m) 0.52-0.56 (4H, m), 1.12-1.20 (2H, m), 2.87-2.88 (2H, d), 2.90-2.91 (2H, d) 3.35-3.42 (2H, t), 3.42-3.69 (2H, t), 7.25-7.29 (1H, d) 7.31-7.32 (1H, d), 7.47-7.50 (1H, d), 7.73-7.75 (1H, d)

MS(m/z): 262

Reaction 3. Synthesis of 2,5-dicyclopropylmethyl naphthylic anhydride 2.35 g (6.8 mmol) of 3,6-dicyclohexylmethyl acenaphthene was added to acetic acid, 10.10 g (33.9 mmol) of sodium dichromate dihydrate was added thereto, and the mixture was stirred at room temperature and heated to reflux. Then, after cooling to room temperature, the reaction mixture was poured into ice water, and after adding ethyl acetate thereto and stirring, the organic layer was separated. The separated organic layer was washed twice with distilled water, and the collected organic layer was dried with anhydrous magnesium sulfate, and the solvent was removed by distillation under reduced pressure. The product obtained by distilling the organic layer under reduced pressure was purified by silica gel column chromatography (developing solvent: ethyl acetate:n-heptane=1:4) to obtain 1.78 g (67.2%) of 2,5-dicyclopropylmethyl naphthylic anhydride.

$^1$H NMR ($\delta_{ppm}$; $CDCl_3$): 0.31-0.36 (4H, m), 0.64-0.70 (4H, m), 1.14-1.23 (2H, m), 3.14-3.16 (2H, d), 3.17-3.19 (2H, d), 7.82-7.86 (2H, m), 8.58-8.60 (1H, d), 8.63-8.65 (1H, d)

MS(m/z): 306

Reaction 4. Synthesis of N-hydroxy-2,5-dicyclopropylmethyl naphthalimide 5.24 g (13.4 mmol) of 2,5-dicyclopropylmethyl naphthylic anhydride was added to ethanol, 1.40 g (20.1 mmol) of hydroxylamine hydrochloride salt and 1.59 g (20.1 mmol) of pyridine were added thereto, and the mixture was heated to reflux. Ethanol was removed under reduced pressure to obtain 3.54 g (crude yield: 65.1%) of crude N-hydroxy-2,5-dicyclopropylmethyl naphthalimide.

$^1$H NMR ($\delta_{ppm}$; $CDCl_3$): 0.30-0.34 (4H, m), 0.64-0.69 (4H, m), 1.12-1.21 (2H, m), 3.14-3.16 (2H, d), 3.17-3.19 (2H, d), 7.81-7.86 (2H, m), 8.62-8.64 (1H, d), 8.67-8.69 (1H, d), 8.71 (1H, b)

MS(m/z): 321

Reaction 5. Synthesis of 2,5-dicyclopropanemethyl-naphthalimide trifluoromethane sulfonate (9)

4.08 g (10.1 mmol) of N-hydroxy-2,5-dicyclopropylmethyl naphthalimide was added to dichloromethane, and 2.04 g (20.1 mmol) of triethylamine was added thereto, and the mixture was stirred for 30 minutes and cooled to 5° C. or lower. After adding 1.70 g (10.1 mmol) of trifluoromethane sulfonyl chloride, the mixture was stirred at room temperature. Then, after adding thereto distilled water and stirring, the organic layer was separated. The separated organic layer was washed twice with distilled water, and the collected organic layer was dried with anhydrous magnesium sulfate, and the solvent was removed by distillation under reduced pressure. The product obtained by distilling the organic layer under reduced pressure was purified by silica gel column chromatography (developing solvent: ethyl acetate:n-heptane=1:4) to obtain 3.52 g (65.1%) of 2,5-dicyclopropanemethyl-naphthalimide trifluoromethane sulfonate (9).

$^1$H NMR ($\delta_{ppm}$; $CDCl_3$): 0.31-0.35 (4H, m), 0.65-0.70 (4H, m), 1.13-1.21 (2H, m), 3.15-3.16 (2H, d), 3.20-3.21 (2H, d), 7.83-7.87 (2H, d), 8.62-8.64 (1H, d), 8.67-8.69 (1H, d)

MS(m/z): 453

The following compounds were prepared in the same manner as in Example 2.

| Compound No. | Structure | 1H-NMR | MS (m/z) |
|---|---|---|---|
| 11 | 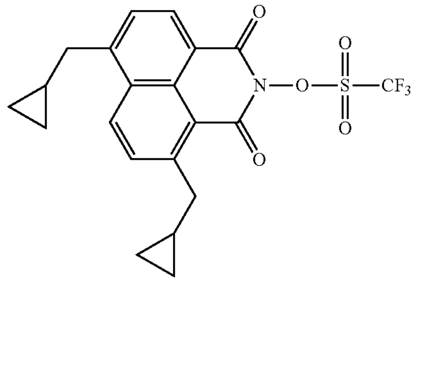 [SMILES: O=C1c2ccc(CC3CC3)c3ccc(CC4CC4)c(c23)C(=O)N1OS(=O)(=O)C(F)(F)F] | 0.31-0.35(4H, m), 0.65-0.70(4H, m), 1.13-1.21(2H, m), 3.15-3.16(2H, d), 3.20-3.21(2H, d), 7.83-7.87(2H, m), 8.62-8.64(1H, d), 8.67-8.69(1H, d) | 453 |

-continued
| Compound No. | Structure | 1H-NMR | MS (m/z) |
|---|---|---|---|
| 12 | 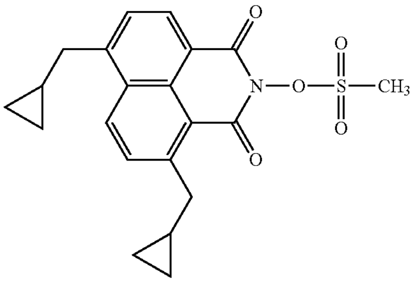 [SMILES: CS(=O)(=O)ON1C(=O)c2ccc(CC3CC3)c3ccc(CC4CC4)c(c23)C1=O] | 0.31-0.35(4H, m), 0.65-0.70(4H, m), 1.13-1.21(2H, m), 3.15-3.16(2H, d), 3.20-3.21(2H, d), 3.52(3H, s), 7.83-7.83-7.87(2H, m), 8.62-8.64(1H, d), 8.67-8.69(1H, d) | 399 |
| 13 | 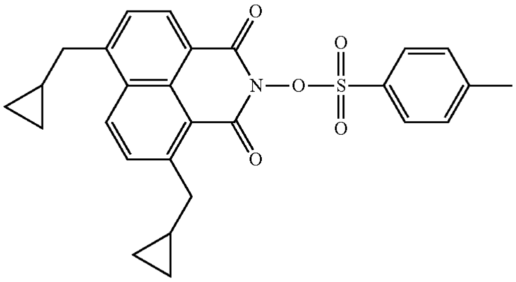 [SMILES: Cc1ccc(S(=O)(=O)ON2C(=O)c3ccc(CC4CC4)c4ccc(CC5CC5)c(c34)C2=O)cc1] | 0.31-0.35(4H, m), 0.65-0.70(4H, m), 1.13-1.21(2H, m), 2.86(3H, s) 3.15-3.16(2H, d), 3.20-3.21(2H, d), 7.48-7.53(2H, d), 7.75-7.80(2H, d), 7.83-7.83-7.87(2H, m), 8.62-8.64(1H, d), 8.67-8.69(1H, d) | 485 |
| 14 | 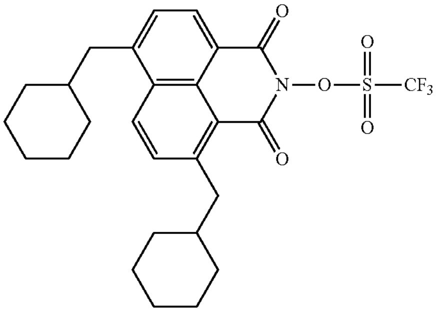 [SMILES: O=C1c2ccc(CC3CCCCC3)c3ccc(CC4CCCCC4)c(c23)C(=O)N1OS(=O)(=O)C(F)(F)F] | 1.06-1.25(10H, m), 1.65-1.71(12H, m), 3.08-3.10(2H, d), 3.13-3.15(2H, d), 7.61-7.63(1H, d), 7.83-7.87(1H, d), 8.59-8.61(1H, d), 8.69-8.71(1H, d) | 538 |
| 15 | 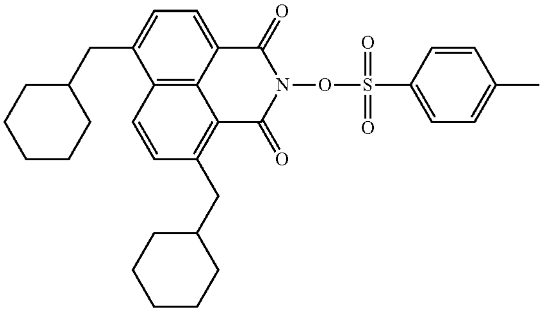 [SMILES: Cc1ccc(S(=O)(=O)ON2C(=O)c3ccc(CC4CCCCC4)c4ccc(CC5CCCCC5)c(c34)C2=O)cc1] | 1.06-1.25(10H, m), 1.65-1.71(12H, m), 2.90(3H,s), 3.08-3.10(2H, d), 3.13-3.15(2H, d), 7.49-7.54(2H, d), 7.75-7.79(2H, d), 7.61-7.63(1H, d), 7.83-7.87(1H, d), 8.59-8.61 (1H, d), 8.69-8.71(1H, d) | 558 |
| 16 | 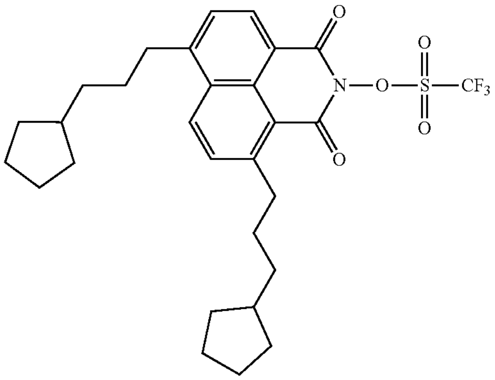 [SMILES: O=C1c2ccc(CCCC3CCCC3)c3ccc(CCCC4CCCC4)c(c23)C(=O)N1OS(=O)(=O)C(F)(F)F] | 1.04-1.12(4H, m), 1.43-1.54(8H, m), 1.54-1.63(4H, m), 1.73-1.85(10H, m), 3.19-3.23(2H, t), 3.28-3.30(2H, t), 7.67-7.68(1H, d), 7.83-7.87(1H, d), 8.60-8.62(1H, d), 8.69-8.71(1H, d) | 565 |

-continued

| Compound No. | Structure | 1H-NMR | MS (m/z) |
|---|---|---|---|
| 17 | 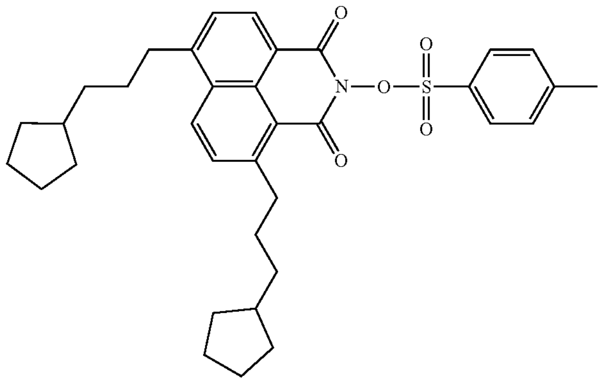 [SMILES: Cc1ccc(S(=O)(=O)ON2C(=O)c3ccc(CCCC4CCCC4)c4ccc(CCCC5CCCC5)c(c34)C2=O)cc1] | 1.04-1.12(4H, m), 1.43-1.54(8H, m), 1.54-1.63(4H, m), 1.73-1.85(10H, m), 3.19-3.23(2H, t), 3.28-3.30(2H, t), 7.49-7.55(2H, d), 7.77-7.80(2H, d), 7.67-7.68(1H, d), 7.83-7.87(1H, d), 8.60-8.62(1H, d), 8.69-8.71(1H, d) | 587 |

Example 3: Preparation of 4-t-butyl acenaphthene (16)

15.00 g (97.3 mmol) of acenaphthene was added to dichloromethane and cooled to 10° C. or lower. 0.65 g (4.9 mmol) of aluminum chloride was added thereto and stirred for 30 minutes, and then 13.33 g (97.3 mmol) of t-butyl bromide was slowly added thereto, and the reaction mixture was heated to reflux and stirred. Next, distilled water was added to the reaction product, and after stirring for 30 minutes, the organic layer was separated. The separated organic layer was washed twice with distilled water, and the collected organic layer was dried with anhydrous magnesium sulfate, and the solvent was removed by distillation under reduced pressure. The concentrated residue was purified by silica gel column chromatography (developing solvent; ethyl acetate:n-heptane=1:4) to obtain 12.03 g (58.8%) of 4-t-butyl acenaphthene (16).

$^1$H NMR ($\delta_{ppm}$; $CDCl_3$): 1.44 (9H, s), 3.32-3.41 (4H, m), 7.11-7.12 (1H, d), 7.29-7.38 (2H, m), 7.76-7.81 (2H, m)

MS(m/z): 210

Example 4: Preparation of 3-t-butyl-5-cyclopropylmethyl-naphthalimide trifluoromethane sulfonate (17)

Reaction 1. Synthesis of 4-t-butyl-6-cyclopropanecarbonyl acenaphthene 5.0 g (23.8 mmol) of 4-t-butyl acenaphthene (16) was added to dichloromethane, and cooled to 10° C. or lower. 3.33 g (25.0 mmol) of aluminum chloride was added thereto and stirred for 30 minutes, and then 2.49 g (23.8 mmol) of cyclopropanecarbonyl chloride diluted in dichloromethane was slowly added thereto, and the reaction mixture was stirred for 1 hour at 5° C. or less. Next, distilled water was added to the reaction product, and after stirring for 30 minutes, the organic layer was separated. The separated organic layer was washed twice with distilled water, and the collected organic layer was dried with anhydrous magnesium sulfate, and the solvent was removed by distillation under reduced pressure. The concentrated residue was purified by silica gel column chromatography (developing solvent; ethyl acetate:n-heptane=1:4) to obtain 4.56 g (68.9%) of 4-t-butyl-6-cyclopropanecarbonyl acenaphthene.

$^1$H NMR ($\delta_{ppm}$; $CDCl_3$): 1.08-1.02 (2H, m), 1.31-1.35 (2H, m), 1.43 (9H, s), 1.50 (9H, s), 2.63-2.74 (1H, m)), 3.40 (4H, m), 7.34-7.36 (1H, d), 7.53-7.54 (1H, d), 8.11-8.13 (1H, d), 8.39-8.40 (1H, d)

MS(m/z): 278

Reaction 2. Synthesis of 4-t-butyl-6-cyclopropylmethyl acenaphthene 5.36 g (19.3 mmol) of 4-t-butyl-6-cyclopropanecarbonyl acenaphthene, 2.60 g (28.9 mmol) of methyl carbazate, and 3.47 g (57.8 mmol) of acetic acid were dissolved in ethanol, and the reaction mixture was heated to reflux. The reaction mixture was then cooled to room temperature and ethanol was removed under reduced pressure. Ethyl acetate and distilled water were added to the concentrated residue, and after stirring, the organic layer was separated. The separated organic layer was washed twice with distilled water, and the collected organic layer was dried with anhydrous magnesium sulfate, and the solvent was removed by distillation under reduced pressure. The product obtained by distilling the organic layer under reduced pressure was added to 5.41 g (96.5 mmol) of potassium hydroxide and triethylene glycol, heated to 140° C., stirred, cooled to room temperature, and stirred with n-heptane and distilled water, and then the organic layer was separated. The separated organic layer was washed twice with distilled water, and the collected organic layer was dried with anhydrous magnesium sulfate, and the solvent was removed by distillation under reduced pressure. The product obtained by distilling the organic layer under reduced pressure was purified by silica gel column chromatography (developing solvent: ethyl acetate:n-heptane=1:10) to obtain 2.66 g (52.3%) of 4-t-butyl-6-cyclopropylmethyl acenaphthene.

$^1$H NMR ($\delta_{ppm}$; $CDCl_3$): 0.23-0.27 (2H, m) 0.52-0.56 (2H, m), 1.12-1.20 (1H, m), 1.50 (9H, s), 2.93-2.94 (2H, d) 3.35-3.42 (4H, m), 7.25-7.26 (1H, d), 7.32-7.33 (1H, d), 7.40-7.41 (1H, d), 7.66-7.67 (1H, d)

MS (m/z): 264

Reaction 3. Synthesis of 3-t-butyl-5-cyclopropylmethyl naphthylic anhydride 10.05 g (38.0 mmol) of 4-t-butyl-6-cyclopropylmethyl acenaphthene was added to acetic acid, 56.63 g (190.0 mmol) of sodium dichromate dihydrate was added thereto, and the mixture was stirred at room temperature and heated to reflux. Then, after cooling to room temperature, ethanol was removed under reduced pressure, and then ethyl acetate and distilled water were added and stirred, and the organic layer was separated. The separated organic layer was washed twice with distilled water, and the collected organic layer was dried with anhydrous magnesium sulfate, and the solvent was removed by distillation under reduced pressure. The product obtained by distilling the organic layer under reduced pressure was purified by silica gel column chromatography (developing solvent: ethyl acetate:n-heptane=1:4) to obtain 7.25 g (61.9%) of 3-t-butyl-5-cyclopropylmethyl naphthylic anhydride.

$^1$H NMR ($\delta_{ppm}$; $CDCl_3$): 0.31-0.36 (2H, m), 0.64-0.70 (2H, m), 1.14-1.23 (1H, m), 1.50 (9H, s), 3.14-3.16 (2H, d), 7.79-7.81 (1H, d), 8.58-8.60 (1H, d), 8.66-8.68 (1H, d), 8.71-8.72 (1H, d)

MS(m/z): 308

Reaction 4. Synthesis of N-hydroxy-3-t-butyl-5-cyclopropylmethyl naphthalimide 10.80 g (35.0 mmol) of 3-t-butyl-5-cyclopropylmethyl naphthylic anhydride was added to ethanol, 3.65 g (52.5 mmol) of hydroxylamine hydrochloride salt and 4.16 g (52.5 mmol) of pyridine were added thereto, and the mixture was heated to reflux. Ethanol was removed under reduced pressure, and then ethyl acetate and distilled water were added and stirred, and the organic layer was separated. The separated organic layer was washed twice with distilled water, and the collected organic layer was dried with anhydrous magnesium sulfate, and the solvent was removed by distillation under reduced pressure. The product obtained by distilling the organic layer under reduced pressure was purified by silica gel column chromatography (developing solvent: ethyl acetate:n-heptane=1:4) to obtain 8.23 g (72.7%) of N-hydroxy-3-t-butyl-5-cyclopropylmethyl naphthalimide.

$^1$H NMR ($\delta_{ppm}$; $CDCl_3$): 0.30-0.34 (2H, m), 0.64-0.69 (2H, m), 1.12-1.21 (1H, m), 1.50 (9H, s), 3.14-3.16 (2H, d), 7.74-7.76 (1H, d), 8.57-8.59 (1H, d), 8.69-8.71 (1H, d) 8.76-8.77 (1H, d), 8.79 (1H, b)

MS(m/z): 323

Reaction 5. Synthesis of 3-t-butyl-5-cyclopropylmethyl-naphthalimide trifluoromethane sulfonate (17)

10.65 g (32.9 mmol) of N-hydroxy-3-t-butyl-5-cyclopropylmethyl naphthalimide was added to dichloromethane, and 6.66 g (65.9 mmol) of triethylamine was added thereto, and the mixture was stirred for 30 minutes and cooled to 5° C. or lower. After adding 5.55 g (32.9 mmol) of trifluoromethane sulfonyl chloride, the mixture was stirred at room temperature. Then, after adding thereto distilled water and stirring, the organic layer was separated. The separated organic layer was washed twice with distilled water, and the collected organic layer was dried with anhydrous magnesium sulfate, and the solvent was removed by distillation under reduced pressure. The product obtained by distilling the organic layer under reduced pressure was purified by silica gel column chromatography (developing solvent: ethyl acetate:n-heptane=1:4) to obtain 10.55 g (70.3%) of 3-t-butyl-5-cyclopropylmethyl-naphthalimide trifluoromethane sulfonate (17).

$^1$H NMR($\delta_{ppm}$; $CDCl_3$): 0.31-0.35 (2H, m), 0.65-0.70 (2H, m), 1.13-1.21 (1H, m), 1.50 (9H, s), 3.15-3.16 (2H, d), 7.77-7.79 (1H, d), 8.61-8.62 (1H, d), 8.70-8.72 (1H, d), 8.77-8.78 (1H, d)

MS(m/z): 455

The following compounds were prepared in the same manner as in Example 4.

| Compound No. | Structure | 1H-NMR | MS (m/z) |
|---|---|---|---|
| 18 | 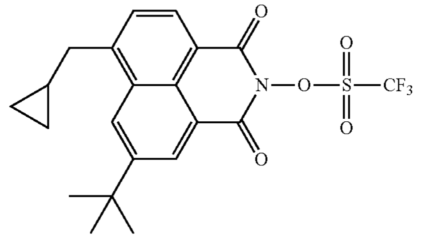 [SMILES: CC(C)(C)c1cc2c3c(ccc(CC4CC4)c3c1)C(=O)N(OS(=O)(=O)C(F)(F)F)C2=O] | 0.31-0.35(2H, m), 0.65-0.70(2H, m), 1.13-1.21(1H, m), 1.50(9H, s), 3.15-3.16(2H, d), 7.77-7.79(1H, d), 8.61-8.62(1H, d), 8.70-8.72(1H, d), 8.77-8.78(1H, d) | 455 |
| 19 | 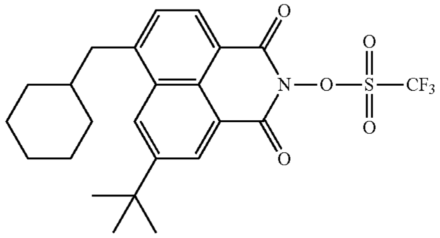 [SMILES: CC(C)(C)c1cc2c3c(ccc(CC4CCCCC4)c3c1)C(=O)N(OS(=O)(=O)C(F)(F)F)C2=O] | 1.06-1.25(5H, m), 1.51(9H, s), 1.65-1.71(6H, m), 3.08-3.10(2H, d), 7.56-7.57(1H, d), 8.58-8.60(1H, d), 8.66-8.68(1H, d), 8.76-8.78(1H, d) | 497 |

-continued

| Compound No. | Structure | 1H-NMR | MS (m/z) |
|---|---|---|---|
| 20 | 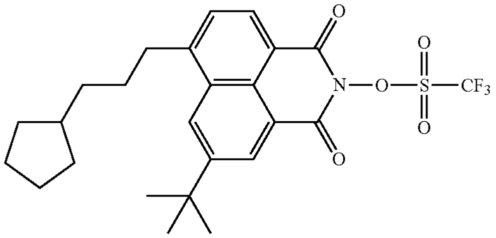 [SMILES: CC(C)(C)c1cc2c3c(ccc(CCCC4CCCC4)c3c1)C(=O)N(OS(=O)(=O)C(F)(F)F)C2=O] | 1.04-1.12(2H, m), 1.43-1.54(13H, m), 1.54-1.63(2H, m), 1.73-1.85(5H, m), 3.19-3.23(2H, t), 7.61-7.63(1H, d), 8.58-8.60(1H, d), 8.68-8.70(1H, d), 8.76-8.78(1H, d) | 511 |

Preparation of Binder Resin a) Preparation of Binder Resin 1

200 ml of propylene glycol monomethyl ether acetate (PGMEA) and 1.5 g of azobisisobutyronitrile (AIBN) were added in a 500 ml polymerization vessel, and acetoxy styrene, styrene, and t-butoxymethacrylate were added with a molar ratio of 50:25:25, respectively, so that the solid content might be 40 weight %, and then polymerized with stirring at 70° C. for 5 hours under nitrogen atmosphere to prepare binder resin 1.

It was confirmed that the weight average molecular weight of the copolymer prepared as such was 25,000, and the degree of dispersion thereof was 2.0.

b) Preparation of Binder Resin 2

200 ml of PGMEA and 1.5 g of AIBN were added in a 500 ml polymerization vessel, and acetoxy styrene, styrene, t-butoxymethacrylate and methyl methacrylate were added with a molar ratio of 40:25:25:10, respectively, so that the solid content might be 40 weight %, and then polymerized with stirring at 70° C. for 5 hours under nitrogen atmosphere to synthesize a copolymer. After adding 0.3 g of N,N-dimethylaniline and 20 molar ratio of glycidyl methacrylate to the reactor, the mixture was stirred at 100° C. for 10 hours to prepare binder resin 2, which was an acrylic polymer having an acrylic unsaturated bond in the side chain. It was confirmed that the weight average molecular weight of the copolymer prepared as such was 20,000, and the degree of dispersion thereof was 2.1.

Measurement of Solubility

In preparing a photoresist composition, solubility of a photoacid generator is very important. Hence, the solubility in propylene glycol monomethyl ether (PGMEA) and cyclohexane, which are solvents mainly used in photoresist compositions, were compared with those of the compound of the following Formula V, and are shown in Table 1 below.

[Formula V]

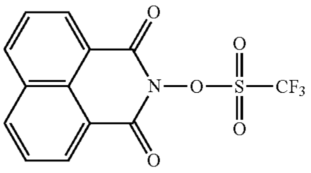

TABLE 1

Solubility of photoacid generators

| Compound No. | Solubility (w/v; %) PGMEA | Cyclohexane |
|---|---|---|
| 1 | 9.2 | 26.1 |
| 5 | 3.1 | 7.8 |
| 9 | 6.3 | 21.3 |
| 13 | 10.2 | 30.2 |
| 19 | 11.0 | 31.2 |
| Formula V | 1.7 | 5.8 |

Measurement of Thermal Stability

If a photoacid generator is thermally stable in a photoresist preparation process, a very good effect in terms of stability can be expected. Hence, the temperature at which 5% weight loss occurred was measured by using a thermogravimetric analyzer to compare with the compound of Formula V.

TABLE 2

Thermal stability of photoacid generators

| Compound No. | Temperature at which 5% weight loss occurred (° C.) |
|---|---|
| 1 | 242 |
| 5 | 252 |
| 9 | 258 |
| 13 | 244 |
| 19 | 236 |
| Formula V | 223 |

Preparation of Photoresist Compositions of Examples

In a reaction mixing bath equipped with an ultraviolet blocking film and an agitator, according to the components and contents shown in Table 3 below, binder resins 1 and 2; compounds 1, 2, 4, 11 and 18 as photoacid generators; and FC-430 (a leveling agent of 3M, 0.02 weight %) were sequentially added, and the mixture was stirred at room temperature, and then PGMEA as a solvent was added to make 100 weight %, to prepare a photoresist composition.

TABLE 3

Preparation of photoresist composition

| Composition No. | Binder resin (parts by weight) | photoacid generator (parts by weight) | Additive (parts by weight) |
|---|---|---|---|
| 1 | 1 (97) | Compound 1 (0.4) | FC-430 (0.1) |
| 2 | 1 (97) | Compound 2 (0.4) | FC-430 (0.1) |

TABLE 3-continued

| Preparation of photoresist composition | | | |
|---|---|---|---|
| Composition No. | Binder resin (parts by weight) | photoacid generator (parts by weight) | Additive (parts by weight) |
| 3 | 1 (97) | Compound 4 (0.4) | FC-430 (0.1) |
| 4 | 1 (97) | Compound 11 (0.4) | FC-430 (0.1) |
| 5 | 1 (97) | Compound 18 (0.4) | FC-430 (0.1) |
| 6 | 2 (97) | Compound 1 (0.4) | FC-430 (0.1) |
| 7 | 2 (97) | Compound 4 (0.4) | FC-430 (0.1) |
| 8 | 2 (97) | Compound 11 (0.4) | FC-430 (0.1) |
| 9 | 2 (97) | Compound 18 (0.4) | FC-430 (0.1) |
| 10 | 2 (97) | Compound 4 (0.4) | FC-430 (0.1) |
| 11 | 1 (60)<br>2 (37) | Compound 1 (0.4) | FC-430 (0.1) |
| 12 | 1 (37)<br>2 (60) | Compound 1 (0.4) | FC-430 (0.1) |

Preparation of Photoresist Composition of Comparative Example

A photoresist composition was prepared in the same manner as in the preparation of Composition 1, except that the photoacid generator of Formula V was used instead of Compound 5 as the photoacid generator.

[Formula V]

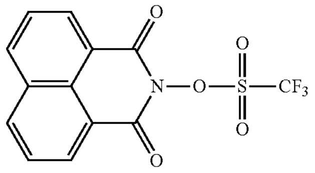

Evaluation of Photoresist Composition

Evaluation of the photoresist compositions of Examples and Comparative Example was performed on a glass substrate, and pattern stability and taper angle of the photoresist composition were measured, and the evaluation results are shown in Table 4 below.

1) Pattern Stability

The photoresist was spin-coated on a silicon wafer substrate, dried on a hot plate at 90° C. for 1 minute, exposed with using a line-space (10 μm-10 μm) step mask, subjected to a post-exposure bake process, and then developed in 2.384% aqueous solution of trimethylammonium hydroxide (TMAH). The width of the pattern in the space portion after the development was measured.

2) Taper Angle

The photoresist was spin-coated on a silicon wafer substrate, dried on a hot plate at 90° C. for 1 minute, exposed with using a line-space (10 μm-10 μm) step mask, subjected to a post-exposure bake process, and then developed in 2.384% aqueous solution of trimethylammonium hydroxide (TMAH). The taper angle of the space portion after the development was measured, and it was determined as good in case of 85 to 90°, and poor in case of less than 85° or greater than 91°.

TABLE 4

| Composition No. | Size of space CD pattern (μm) | Value compared with Comparative Example | Condition of taper angle |
|---|---|---|---|
| 1 | 12.4 | 1.07 | Good |
| 2 | 11.4 | 0.98 | Poor |

TABLE 4-continued

| Composition No. | Size of space CD pattern (μm) | Value compared with Comparative Example | Condition of taper angle |
|---|---|---|---|
| 3 | 12.4 | 1.07 | Good |
| 4 | 12.5 | 1.08 | Good |
| 5 | 11.8 | 1.02 | Good |
| 6 | 12.4 | 1.07 | Good |
| 7 | 12.3 | 1.06 | Good |
| 8 | 12.0 | 1.03 | Good |
| 9 | 12.4 | 1.07 | Good |
| 10 | 12.3 | 1.06 | Good |
| 11 | 12.0 | 1.03 | Good |
| 12 | 12.0 | 1.03 | Good |
| Comparative Example | 11.6 | 1.00 | Poor |

The invention claimed is:

1. A naphthalimide sulfonic acid derivative compound represented by the following Formula I or II:

[Formula I]

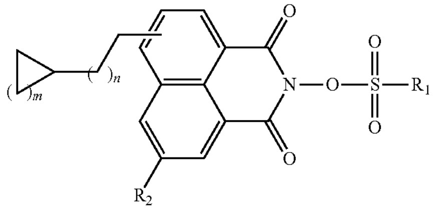

wherein, in Formula I, $R_1$ is a substituted or unsubstituted aliphatic hydrocarbon group, a substituted or unsubstituted aryl group, a substituted or unsubstituted arylalkyl group, or a substituted or unsubstituted alkylaryl group; $R_2$ is hydrogen atom or t-butyl group;

m is an integer of 1 to 4; n is an integer of 0 to 2;

[Formula II]

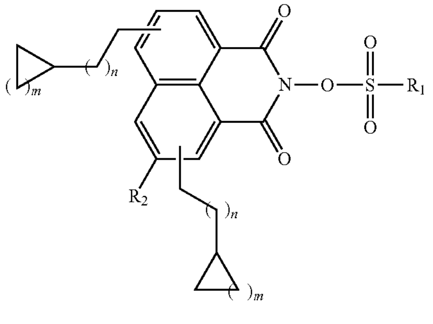

wherein, in Formula II, $R_1$, m and n are the same as defined in Formula I, and $R_2$ is hydrogen atom.

2. The naphthalimide sulfonic acid derivative compound of claim 1, wherein $R_1$ is a $C_1$-$C_{12}$ linear alkyl group or $C_3$-$C_{12}$ branched alkyl group that is unsubstituted or substituted with one or more halogen atoms or alicyclic hydrocarbon group; a $C_3$-$C_{12}$ alicyclic hydrocarbon group that is unsubstituted or substituted with one or more halogen atoms; a $C_6$-$C_{20}$ aryl group that is unsubstituted or substituted with one or more halogen atoms; a $C_7$-$C_{20}$ arylalkyl group that is unsubstituted or substituted with one or more halogen atoms or $C_1$-$C_{12}$ alkylthio group; or a $C_7$-$C_{20}$ alkylaryl group that is unsubstituted or substituted with one or more halogen atoms.

3. The naphthalimide sulfonic acid derivative compound of claim 1, wherein $R_1$ is methyl group, ethyl group, trifluoromethyl group, 2,2,2-trifluoroethyl group, nonafluorobutyl group or tosyl group.
4. The naphthalimide sulfonic acid derivative compound of claim 1, which is selected from the following compounds:
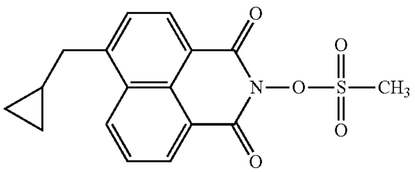
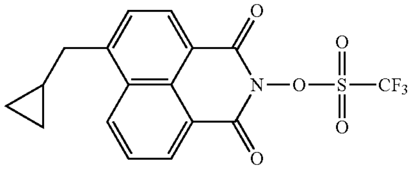
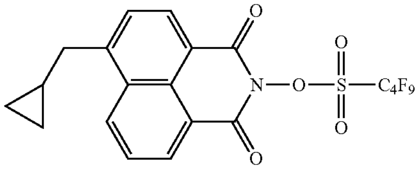
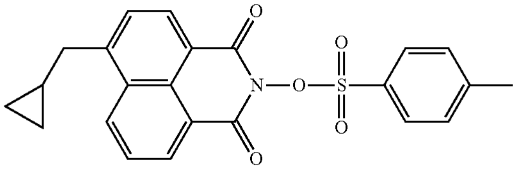
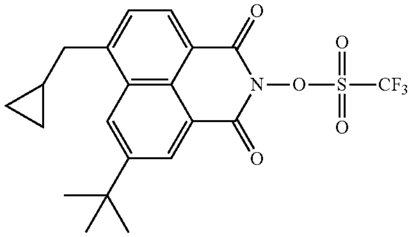
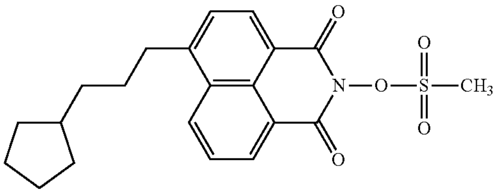
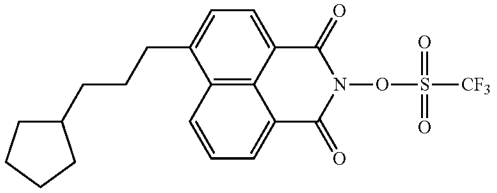
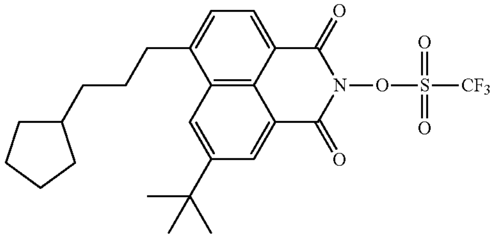
-continued
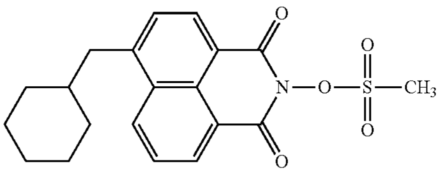
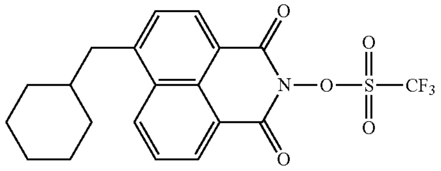
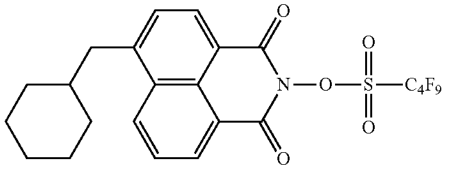
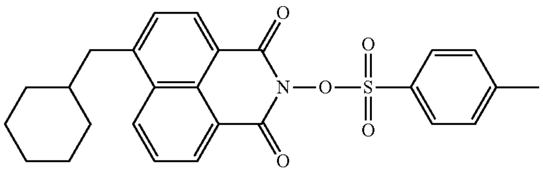
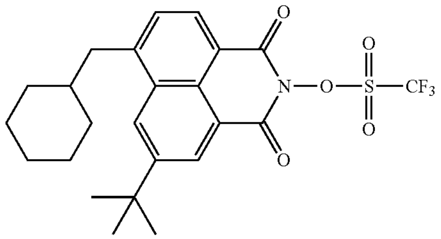
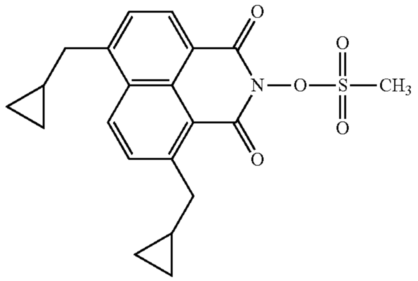
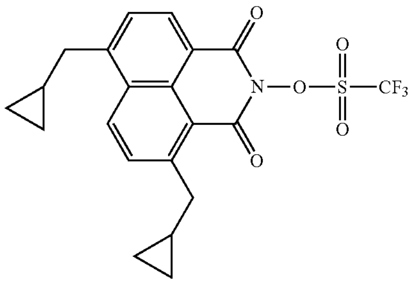

-continued
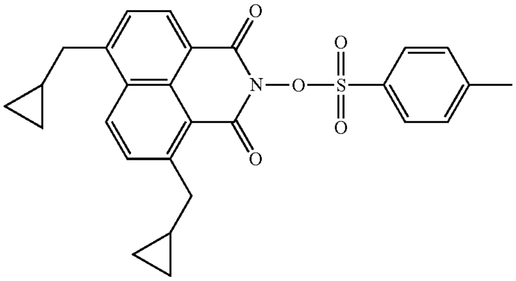
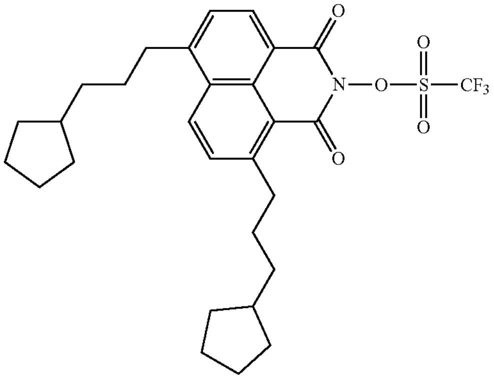
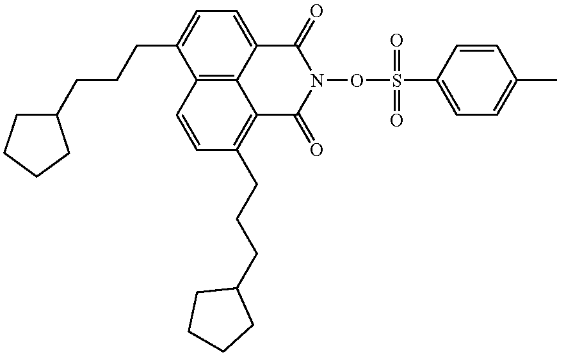
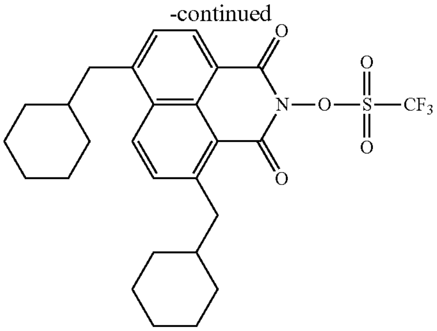
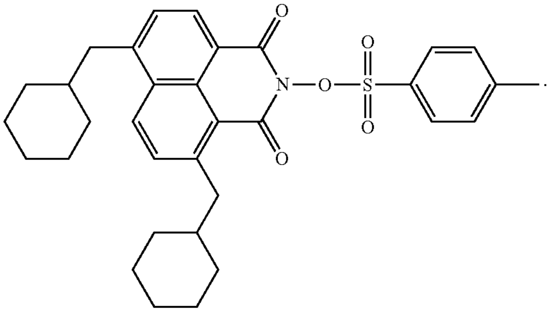
5. A photoacid generator comprising a naphthalimide sulfonic acid derivative compound of claim 1.
6. A photoresist composition comprising a naphthalimide sulfonic acid derivative compound of claim 1; and a binder resin.
* * * * *